(12) United States Patent
Bonde-Larsen et al.

(10) Patent No.: US 9,682,984 B2
(45) Date of Patent: Jun. 20, 2017

(54) METHODS FOR THE PREPARATION OF ALCAFTADINE

(71) Applicant: Crystal Pharma S.A.U., Boecillo (ES)

(72) Inventors: Antonio Lorente Bonde-Larsen, Boecillo (ES); Jesús Miguel Iglesias Retuerto, Boecillo (ES); Franciso Javiér Gallo Nieto, Boecillo (ES); Juan José Ferreiro Gil, Boecillo (ES)

(73) Assignee: Crystal Pharma S.A.U., Boecillo (ES)

( * ) Notice: Subject to any disclaimer, the term of this patent is extended or adjusted under 35 U.S.C. 154(b) by 0 days.

(21) Appl. No.: 14/778,461

(22) PCT Filed: Mar. 24, 2014

(86) PCT No.: PCT/EP2014/055815
§ 371 (c)(1),
(2) Date: Sep. 18, 2015

(87) PCT Pub. No.: WO2014/154620
PCT Pub. Date: Oct. 2, 2014

(65) Prior Publication Data
US 2016/0280709 A1   Sep. 29, 2016

(30) Foreign Application Priority Data

Mar. 25, 2013 (EP) .................... 13160829

(51) Int. Cl.
*C07D 487/04* (2006.01)

(52) U.S. Cl.
CPC .................... *C07D 487/04* (2013.01)

(58) Field of Classification Search
CPC .................... C07D 487/04
USPC .................... 540/579
See application file for complete search history.

(56) References Cited

FOREIGN PATENT DOCUMENTS

| | | |
|---|---|---|
| EP | 0 518 435 A1 | 12/1992 |
| EP | 0 588 858 A1 | 3/1994 |
| WO | WO 92/22551 A1 | 12/1992 |

OTHER PUBLICATIONS

International Search Report for PCT/EP2014/055815 dated May 12, 2014.

*Primary Examiner* — Brenda Coleman
(74) *Attorney, Agent, or Firm* — Knobbe Martens Olson & Bear LLP

(57) ABSTRACT

The invention relates to new and improved processes for the preparation of Alcaftadine and pharmaceutically acceptable salts thereof as well as an intermediate for the preparation of Alcaftadine. The new process saves a number of steps compared to the known process and results in a higher yield.

15 Claims, No Drawings

METHODS FOR THE PREPARATION OF ALCAFTADINE

CROSS REFERENCE TO RELATED APPLICATIONS

This application is a U.S. National Phase Application of PCT International Application Number PCT/EP2014/055815, filed on Mar. 24, 2014, designating the United States of America and published in the English language, which is an International Application of and claims the benefit of priority to European Patent Application No. 13160829.1, filed on Mar. 25, 2013. The disclosures of the above-referenced applications are hereby expressly incorporated by reference in their entireties.

FIELD OF THE INVENTION

The present invention relates to new and improved processes for the preparation of Alcaftadine and pharmaceutically acceptable salts thereof as well as an intermediate for the preparation of Alcaftadine.

BACKGROUND OF THE INVENTION

The compound 6,11-dihydro-11-(1-methyl-4-piperidinylidene)-5H-imidazo[2,1-b][3]benzazepine-3-carboxaldehyde, which is known as Alcaftadine (INN), and its corresponding salts are H1 histamine receptor antagonists indicated for the prevention of itching associated with allergic conjunctivitis and is sold commercially as an ophthalmic solution containing Alcaftadine (0.25%) under the trade name Lastacaft.

EP 0 588 858 describes the preparation of Alcaftadine for the first time through the process:

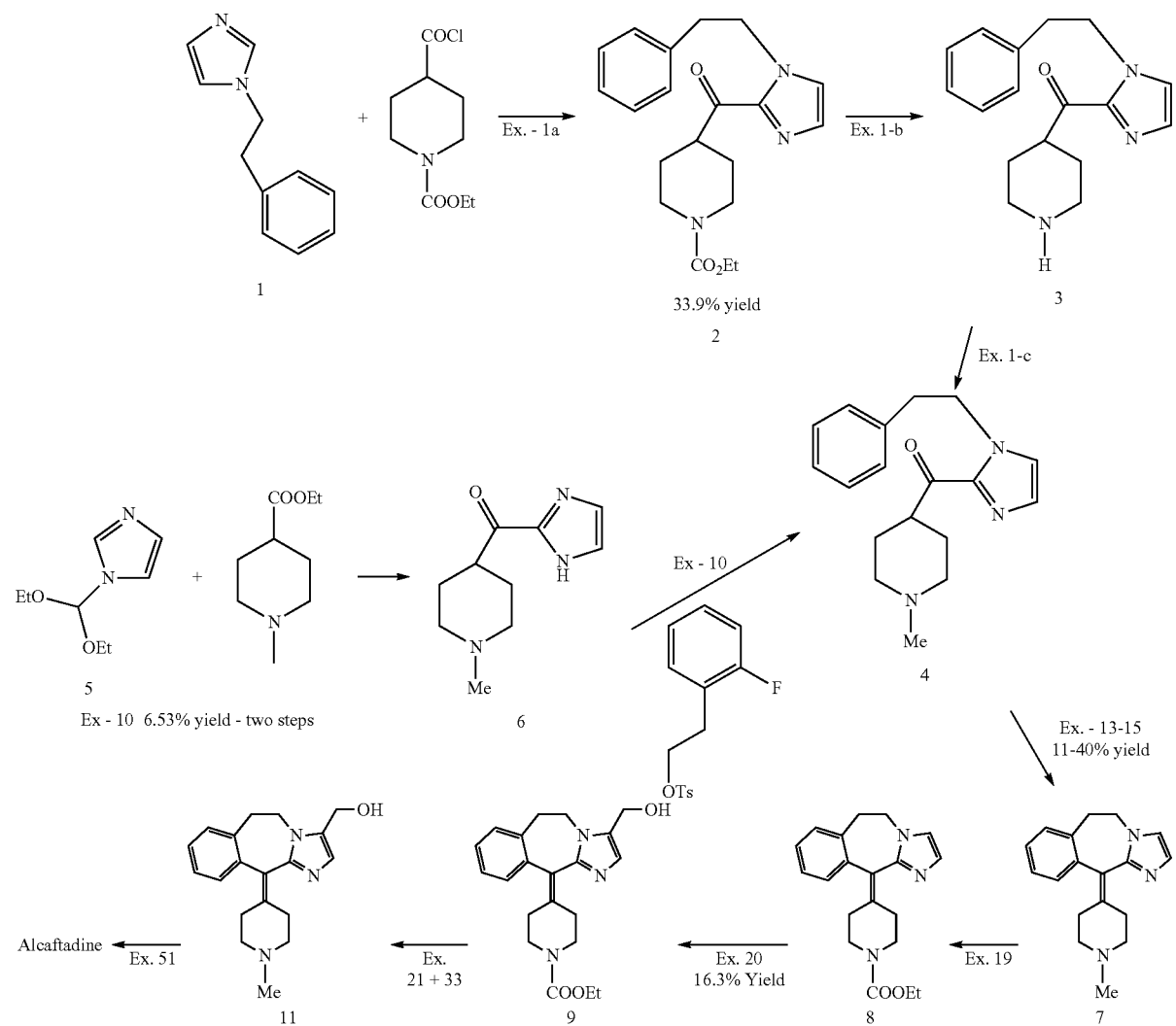

It is evident that a number of steps are needed in EP 0 588 858 to arrive at the intermediate of formula 7 (free base) from the starting compound of formula 1 with a relatively low yield. Furthermore, the introduction in the intermediate of formula 7 (free base) of the hydroxymethyl substituent and subsequent oxidation to arrive at Alcaftadine requires a cumbersome, low-yield protection and de-protection process, using an ethylcarboxylate protecting group.

In addition, the introduction of the hydroxymethyl group requires stirring with 22 equivalents of formaldehyde for at least 1 week according to example 20a) of EP 0 588 858. Long reaction times furthermore increase the risk of obtaining the dihydroxymethyl impurity (example 20b)).

There exists, therefore, the need to develop an improved process for obtaining Alcaftadine and salts thereof, which overcomes some or all of the problems associated with known methods from the state of the art. More particularly, there exists the need for a process for obtaining Alcaftadine and pharmaceutically acceptable salts thereof, which results in a higher yield and/or having fewer reaction steps.

SUMMARY OF THE INVENTION

In one aspect of the invention, it concerns a process for preparing Alcaftadine or a pharmaceutically acceptable salt thereof reacting the acid addition salt of formula 7 with formaldehyde to the compound of formula 11 or a salt thereof and then oxidizing the compound of formula 11 or a salt thereof to Alcaftadine:

days. This, in turn, decreases the risk of introducing a second hydroxymethyl group into the compound in a quantitative amount.

A further aspect of the invention concerns a process for the preparation of Alcaftadine or a pharmaceutically acceptable salt thereof comprising reacting a compound of formula 1 with ethyl 1-methylpiperidine-4-carboxylate in the presence of a strong base to provide a compound of formula 4, which is further reacted with trifluoromethanesulfonic acid and subsequently a di-carboxylic acid, HA, as defined above to provide the acid addition salt of formula 7:

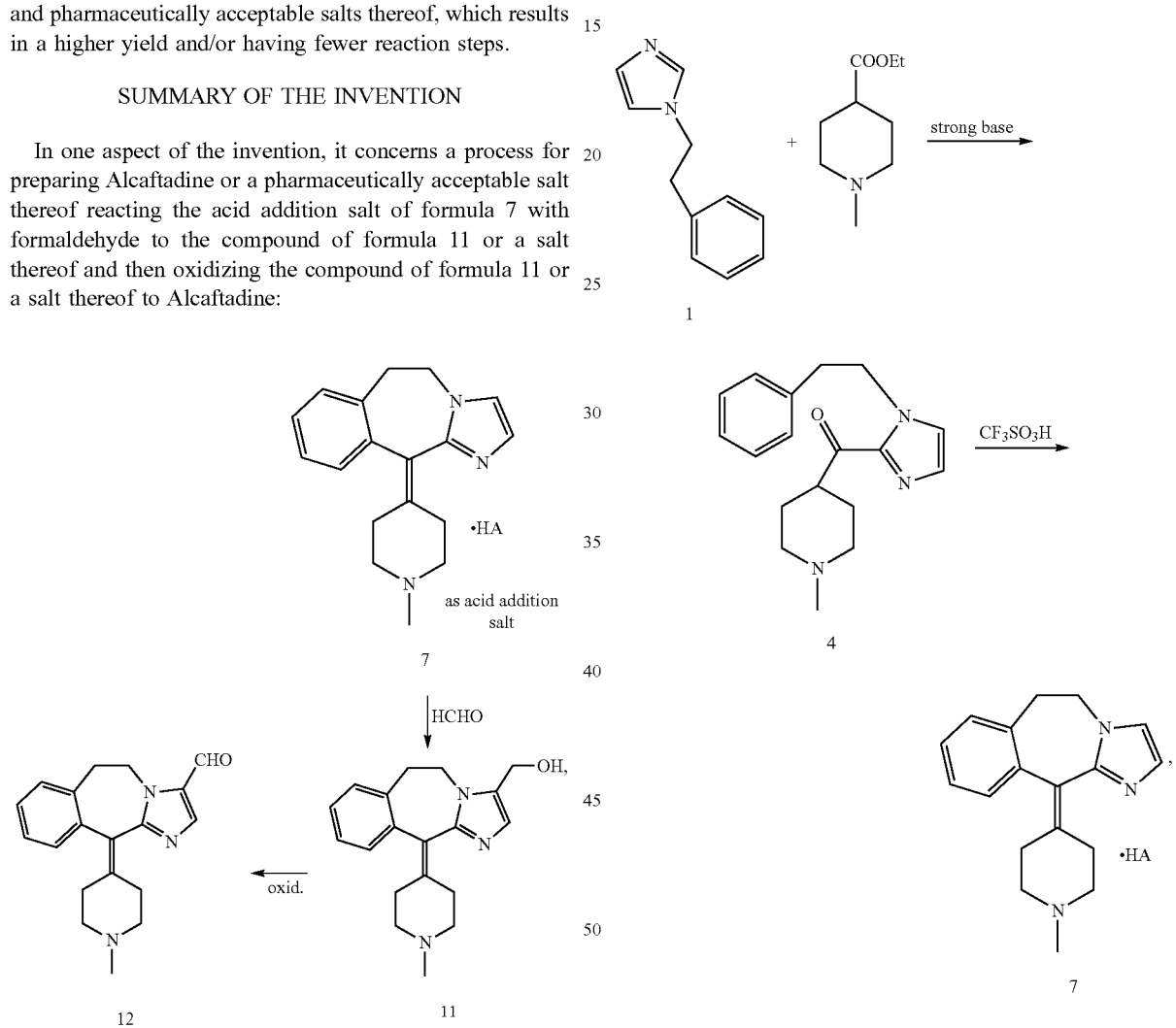

and further reacting the acid addition salt of formula 7 to provide Alcaftadine or, optionally, a pharmaceutically acceptable salt thereof.

The method herein provides Alcaftadine in a yield and purity superior to the methods known in the art. Furthermore, it has been found that careful selection of crystallization solvents will provide Alcaftadine in a purity higher than 99%. Hence, yet a further aspect of the invention concerns a process for the isolation and purification of Alcaftadine comprising crystallization in isopropyl alcohol or ethyl acetate.

and optionally converting Alcaftadine to a pharmaceutically acceptable salt thereof,
wherein the acid addition salt of formula 7 is a salt formed with a di-carboxylic acid, HA, such as fumaric acid, maleic acid, succinic acid, or tartaric acid.

This process converts the acid addition salt of formula 7 directly to the compound of formula 11 without the need for protecting with ethyl carboxylate and therefore saves three reaction steps. Furthermore, the yield is significantly increased and the reaction time for introducing the hydroxymethyl group has been reduced to less than two In another aspect of the invention, it concerns an acid addition salt of formula 7:

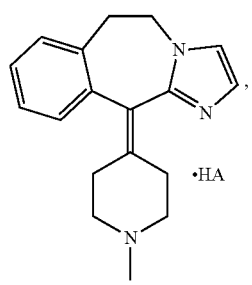

wherein the di-carboxylic acid, HA, is as defined above.

The neutral form of the acid addition salt of formula 7 is known from EP 0 588 858, but the acid addition salt of formula 7 is a novel compound.

DETAILED DESCRIPTION OF THE INVENTION

Definitions

In the present context, the term "strong base" is intended to mean a base sufficiently strong to remove a hydrogen from position 2 of the imidazole ring in the compound of formula 1. Such bases are well known to the person skilled in the art and include inter alia lithium diisopropylamide, hexyl-lithium, butyl-lithium, and lithium hexamethyldisilazide.

In the present context, when referring to "the acid addition salt of formula 7", "compound of formula 7" or "intermediate 7", it is intended to mean the acid addition salt and not the free base, unless explicitly referred to as the free base or the context otherwise makes it clear that the free base is meant.

In the present context, the term "di-carboxylic acid" is intended to mean an organic acid with two or more carboxylic acid groups and a total of 2 to 10 carbon atoms in the molecule. Thus, the term "di-carboxylic acid" includes, by way of example, oxalic acid, malonic acid, succinic acid, glutaric acid, adipic acid, pimelic acid, suberic acid, azelaic acid, sebacic acid, tartaric acid, EDTA, citric acid, fumaric acid, maleic acid, glutaconic acid, muconic acid, phthalic acid, isophthalic acid, terephthalic acid, and malic acid.

Processes

In one aspect of the invention, it concerns a process for preparing Alcaftadine or a pharmaceutically acceptable salt thereof reacting the acid addition salt of formula 7 with formaldehyde, optionally in the presence of a base, to the compound of formula 11 or a salt thereof and then oxidizing the compound of formula 11 or a salt thereof to Alcaftadine:

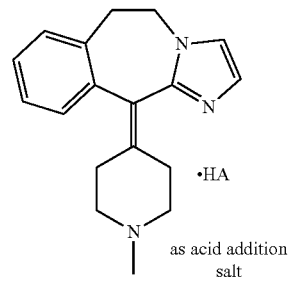

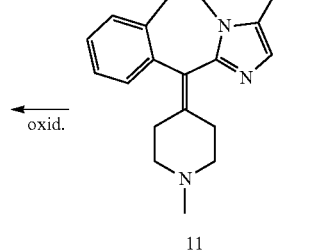

and optionally converting Alcaftadine to a pharmaceutically acceptable salt thereof, wherein the acid addition salt of formula 7 is a salt formed with a di-carboxylic acid, HA, such as fumaric acid, maleic acid, succinic acid, or tartaric acid.

In one embodiment, the acid addition salt of formula 7 is formed by reacting the compound of formula 1 with ethyl 1-methylpiperidine-4-carboxylate in the presence of a strong base to provide a compound of formula 4, which is further reacted with trifluoromethanesulfonic acid and subsequently a di-carboxylic acid, HA, as defined above to provide the acid addition salt of formula 7:

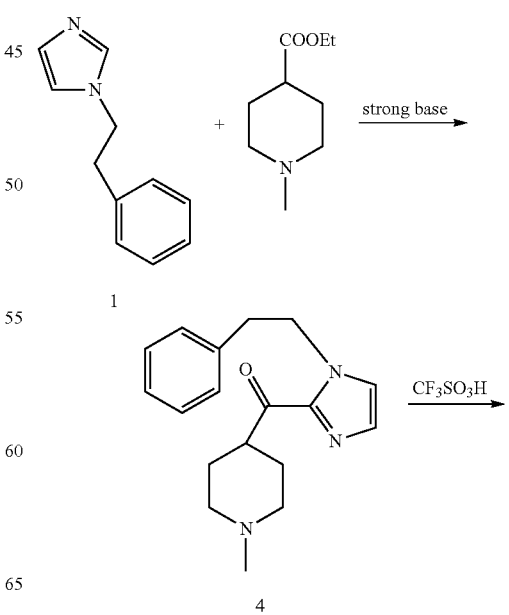

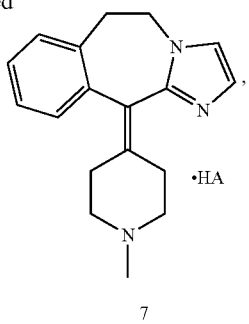

7

In a further embodiment, said strong base is lithium diisopropylamide or hexyl lithium.

A further aspect of the invention concerns a process for the preparation of Alcaftadine or a pharmaceutically acceptable salt thereof comprising reacting a compound of formula 1 with ethyl 1-methylpiperidine-4-carboxylate in the presence of a strong base to provide a compound of formula 4, which is further reacted with trifluoromethanesulfonic acid and subsequently a di-carboxylic acid, HA, as defined above to provide the acid addition salt of formula 7:

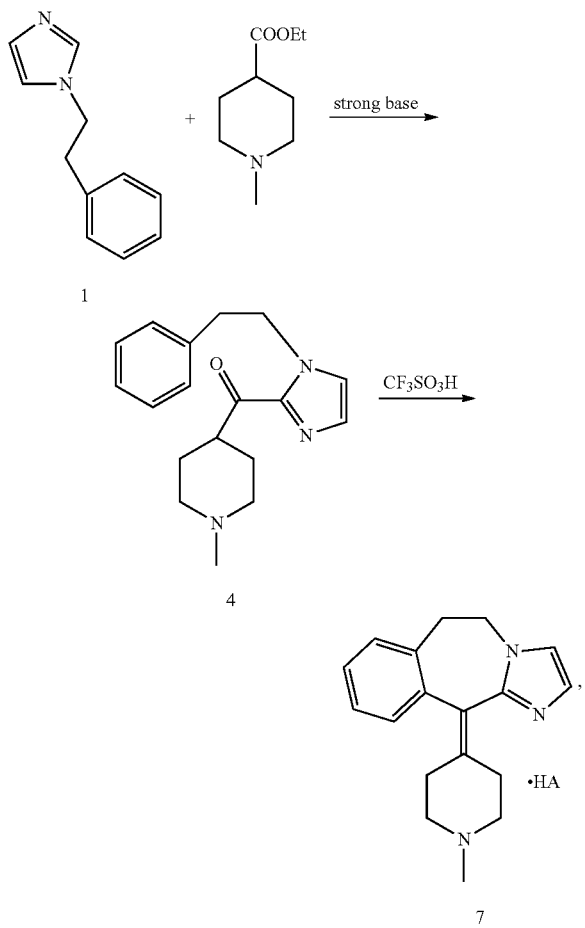

and further reacting the acid addition salt of formula 7 to provide Alcaftadine or, optionally, a pharmaceutically acceptable salt thereof.

In one embodiment, said strong base is lithium diisopropylamide or hexyl lithium.

Yet a further aspect of the invention concerns a process for the isolation and purification of Alcaftadine comprising crystallization in isopropyl alcohol or ethyl acetate.

In another aspect of the invention, it concerns an acid addition salt of formula 7:

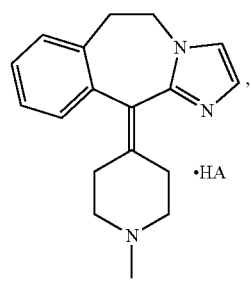

7 wherein the di-carboxylic acid, HA, is as defined above.

The Di-Carboxylic Acid

The di-carboxylic acid serves a double function in that it both facilitates the purification of the acid addition salt of formula 7 by crystallization and at the same time provides a much better starting point for introducing the hydroxymethyl group into the molecule than the corresponding neutral compound. The corresponding reaction from the corresponding neutral base to the compound of formula 11 lasts at least 1 week, whereas taking the acid addition salt of formula 7 as the starting point means that the reaction only needs about 20 to 40 hours to complete.

The di-carboxylic acid may in one embodiment be selected from the group consisting of oxalic acid, malonic acid, succinic acid, glutaric acid, adipic acid, pimelic acid, suberic acid, azelaic acid, sebacic acid, tartaric acid, EDTA, citric acid, fumaric acid, maleic acid, glutaconic acid, muconic acid, phthalic acid, isophthalic acid, terephthalic acid, and malic acid. In another embodiment, said di-carboxylic acid is selected from the group consisting of fumaric acid, maleic acid, succinic acid, and tartaric acid. In a further embodiment, said di-carboxylic acid is fumaric acid or succinic acid. In yet a further embodiment, said di-carboxylic acid is fumaric acid. In still a further embodiment, said di-carboxylic acid is succinic acid.

Oxidation Reagents

The skilled person is familiar with the oxidation reagents used in the art for selectively oxidizing primary alcohols to the corresponding aldehyde. These oxidation reagents include chromium-based reagents, such as Collins reagent ($CrO_3.Py_2$), pyridinium dichromate, or pyridinium chlorochromate; activated DMSO, resulting from reaction of DMSO with electrophiles, such as oxalyl chloride (Swern oxidation), a carbodiimide (Pfitzner-Moffatt oxidation) or the complex $SO_3.Py$ (Parikh-Doering oxidation); hypervalent iodine compounds, such as Dess-Martin periodinane or 2-Iodoxybenzoic acid; catalytic tetrapropylammonium perruthenate in the presence of excess of N-methylmorpholine N-oxide (Ley oxidation); catalytic TEMPO in the presence of excess sodium hypochlorite (Anelli's oxidation); or manganese dioxide.

In one embodiment, the oxidation reagent in the reaction from the compound of formula 11 to the compound of formula 12 (Alcaftadine) is manganese dioxide, $MnO_2$.

The Reaction Forming the Compound of Formula 4

The starting compounds, the compound of formula 1 (CAS number 49823-14-5) and 1-methylpiperidine-4-carboxylate (CAS number 24252-37-7), are commercially available.

The reaction between the compound of formula 1 and 1-methylpiperidine-4-carboxylate is carried out in the presence of a strong base, as defined above. The bases meeting this definition are well known to the skilled person and include hexyl-lithium, butyl-lithium, lithium hexamethyldisilazide, and sodium hydride. In one embodiment, said strong base is lithium diisopropylamide.

The reaction temperature is advantageously kept in the range −80° C. to −30° C., such as in the range −80° C. to −40° C., e.g. in the range −80° C. to −60° C.

In order to avoid build-up of impurities during the reaction, it is advantageous to add between 1 and 3 equivalents of 1-methylpiperidine-4-carboxylate, such as between 1.5 and 2.6 equivalents. Hence, in one embodiment 1 to 3 equivalents of 1-methylpiperidine-4-carboxylate are added to the compound of formula 1. In another embodiment, 1.5 to 2.6 equivalents of 1-methylpiperidine-4-carboxylate are added to the compound of formula 1.

The reaction solvent used is advantageously an aprotic solvent. In one embodiment, the solvent is tetrahydrofuran, toluene, or a mixture thereof.

The resulting product, the compound of formula 4, may be isolated in acetone, ethyl acetate, or dichloromethane in the form of the hydrochloride or the hydrobromide.

The overall yield of the reaction is up to 85%.

The Reaction Forming the Acid Addition Salt of Formula 7

The ring closure of the compound of formula 4 may be achieved by adding trifluoromethanesulfonic acid as the only acid component. Advantageously, the reaction is carried out at a temperature between 70 and 130° C. using 4 to 20 volumes of trifluoromethanesulfonic acid. Hence, in one embodiment, the reaction is carried out at a temperature between 70 and 130° C., such as a temperature between 90 and 130° C., e.g. between 110 and 130° C. In another embodiment, the reaction is carried out using between 4 and 20 volumes of trifluoromethanesulfonic acid, such as between 10 and 20 volumes, e.g. between 15 and 20 volumes.

The resulting product may be purified by crystallization by adding the di-carboxylic acid, HA, to form the acid addition salt of formula 7. Suitable solvents for the crystallization include acetone, methanol, ethyl acetate, isopropyl alcohol, and mixtures thereof. In one embodiment, said solvent for the crystallization of the acid addition salt of formula 7 is selected from acetone, isopropyl alcohol, and mixtures thereof.

The Reaction Forming the Compound of Formula 11

The acid addition salt of formula 7 may be used as the starting point in purified or non-purified form. In both cases, the reaction time is reduced considerably compared to taking the corresponding neutral base as the starting point, even if the neutral compound is in purified form.

The reaction between the acid addition salt of formula 7 and formaldehyde is advantageously carried out with heating, such as at a temperature between 80 and 100° C., in an aqueous solvent or in combination with an organic solvent such as Toluene, Xylene or heptane.

Furthermore, the reaction between the acid addition salt of formula 7 and formaldehyde is advantageously carried out in the presence of a base. However, the reaction carried out without the presence of a base is still considerably more efficient than the corresponding reaction carried out with the neutral form of the acid addition salt of formula 7 (comparative example 12). In one embodiment, said base is selected from the group consisting of carboxylate, such as acetate; carbonate or bicarbonate; pyridine; and benzyltrimethylammonium hydroxide. In a further embodiment, said base is a carboxylate or bicarbonate. In yet a further embodiment, said base is acetate. In yet a further embodiment, said base is sodium acetate. In still a further embodiment, said base is sodium acetate, sodium bicarbonate or pyridine.

The overall yield of the reaction is 70-75%. The yield and purity of the direct product of the reaction, the compound of formula 11, facilitates its purification on an industrial scale, such as by crystallization of the fumarate salt in acetone as solvent or by crystallization of the succinate salt in Ethyl acetate as solvent. Acetonitrile is a suitable solvent for the crystallization of the compound of formula 11 as a base.

The Oxidation of the Compound of Formula 11

The reaction conditions for the oxidation reaction may depend on the chosen oxidation reagent. In the case of manganese dioxide, the reaction may be carried out under similar circumstances as those disclosed in EP 0 588 858 (example 51).

Purification of Alcaftadine

The product (Alcaftadine) may be isolated and purified from solvents such as isopropanol, ethyl acetate, or isopropyl ether. Isopropanol and ethyl acetate may advantageously be used as solvents for the purification with a final yield of 50-65%.

Hence, yet a further aspect of the invention concerns a process for the isolation and purification of Alcaftadine comprising crystallization in isopropyl alcohol or ethyl acetate.

Pharmaceutically Acceptable Salts

Pharmaceutically acceptable acid addition salts of Alcaftadine are easily identified by the skilled person. A useful list of pharmaceutically acceptable acid addition salts may be found in Berge et al: "Pharmaceutical Salts", Journal of Pharmaceutical Sciences, vol. 66, no. 1, 1 Jan. 1977, pages 1-19.

Intermediate Compounds

The process of the invention involves a novel intermediate, which has not previously been used in the preparation of Alcaftadine. Hence, a further aspect of the invention concerns the acid addition salt of formula 7.

EXAMPLES

Example 1

Preparation of [1-(2-phenylethyl)-1H-imidazol-2-yl] (1-methyl-4-piperidinyl)-methanone (intermediate 4)

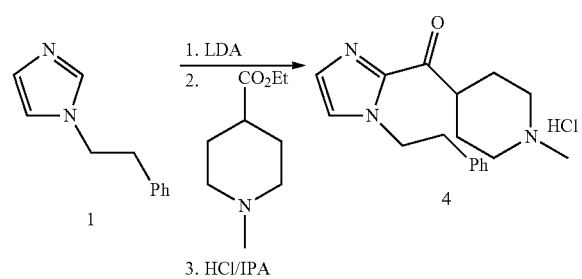

N-(2-phenyl)-ethyl imidazole (20 g, 0.12 mol) was dissolved in a mixture of toluene (100 ml) and tetrahydrofuran (60 ml). The solution formed was cooled down to −50° C. and then a solution of LDA (lithium diisopropylamide) 2 M in tetrahydrofuran (128 ml, 0.26 mol) was added. The temperature was kept at −50° C. for 15 minutes and then a solution of N-methyl ethyl isonipecotate (48.1 g, 0.28 mol) in toluene (50 ml) was added. After 1 hour at −50° C. the reaction was quenched by addition of water (200 ml).

The temperature was adjusted to 20° C. and the layers were separated. The aqueous layer was extracted with toluene and the solvents were distilled to a final volume of 60 ml.

A 5-6 N solution of HCl in isopropanol (74 ml) was added followed by acetone 1200 ml. The solid formed was filtered, washed with acetone (100 ml) and dried to afford 28.5 g (74% yield) of [1-(2-phenylethyl)-1H-imidazol-2-yl](1-methyl-4-piperidinyl)-methanone (intermediate 4) as the hydrochloride salt.

Spectroscopic Data of Intermediate 4 (Hydrochloride Salt):
$^1$H-NMR (400 MHz, DMSO-d6), δ: 1.80-2.00 (4H, m), 2.67 (3H, d, J=4.8 Hz), 2.95 (2H, t, J=7.2 Hz), 2.95-3.10 (2H, m), 3.39 (2H, d, J=11.2 Hz), 3.70-3.80 (1H, m), 4.56 (2H, t, J=7.2 Hz), 7.13 (1H, s), 7.15-7.25 (5H, m), 7.50 (1H, s), 11.0 (1H, broad s).
$^{13}$C-NMR (100 MHz, DMSO-d6), δ: 25.4 (2×CH$_2$), 36.7 (CH$_2$), 41.0 (CH), 42.5 (CH$_3$), 49.0 (CH$_2$), 52.3 (2×CH$_2$), 126.5 (CH), 127.6 (CH), 128.4 (2×CH), 128.7 (2×CH), 137.6 (C), 137.7 (C), 140.3 (C), 191.9 (C=O)

A sample of the solid (1 g) was dissolved in dichloromethane and water and the pH was adjusted to 9-10 with 50% aqueous NaOH. The product was extracted with dichloromethane and the solvent was distilled off to afford 0.85 g of [1-(2-phenylethyl)-1H-imidazol-2-yl](1-methyl-4-piperidinyl)-methanone (intermediate 4) (free base) as a colourless oil.

Spectroscopic Data of Intermediate 4 (Free Base):
$^1$H-NMR (400 MHz, DMSO-d6), δ: 1.56 (2H, dq, J=3.6, 12.4 Hz), 1.71 (1H, d, J=12.0 Hz), 1.87 (1H, t, J=11.2 Hz), 2.11 (3H, s), 2.75 (1H, d, J=11.2 Hz), 2.94 (2H, t, J=7.2 Hz), 3.50 (1H, tt, J=3.6, 12.0 Hz), 4.55 (2H, t, J=7.2 Hz), 7.04 (1H, s), 7.10-7.25 (5H, m), 7.36 (1H, s).
$^{13}$C-NMR (100 MHz, DMSO-d6), δ: 28.1 (2×CH$_2$), 36.8 (CH$_2$), 43.3 (CH), 46.1 (CH$_3$), 48.9 (CH$_2$), 54.8 (2×CH$_2$), 126.3 (CH), 126.9 (CH), 128.2 (2×CH), 128.6 (2×CH), 137.7 (C), 141.1 (C), 194.3 (C=O).

Example 2

Preparation of [1-(2-phenylethyl)-1H-imidazol-2-yl](1-methyl-4-piperidinyl)-methanone (intermediate 4) as the hydrobromide salt

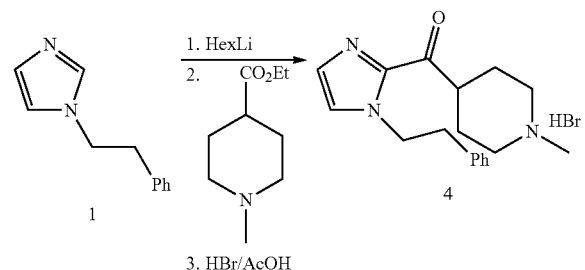

N-(2-phenyl)-ethyl imidazole (7.9 g, 0.046 mol) was dissolved in a mixture of toluene (40 ml) and tetrahydrofuran (24 ml). The solution formed was cooled down to −50° C. and then a solution of hexyllithium 2.7 M in hexane (37.5 ml, 0.101 mol) was added. The temperature was kept at −50° C. for 15 minutes and then a solution of N-methyl ethyl isonipecotate (19.0 g, 0.11 mol) in toluene (20 ml) was added. After 1 hour at −50° C. the reaction was quenched by addition of water (80 ml).

The temperature was adjusted to 20° C. and the layers were separated. The aqueous layer was extracted with toluene and the solvents were distilled to a final volume of 24 ml.

A 33% solution of HBr in acetic acid (7.8 ml) was added followed by ethyl acetate (160 ml). The solid was filtered, washed with ethyl acetate (40 ml) and dried to afford 11.6 g (67% yield) of intermediate 4 as the hydrobromide salt.
Spectroscopic data of intermediate 4 (hydrobromide salt):
$^1$H-NMR (400 MHz, DMSO-d6), δ: 1.80 (2H, m, J=12.4 Hz), 1.98 (2H, d, J=12.0 Hz), 2.75 (3H, d, J=4.8 Hz), 2.95 (2H, t, J=7.2 Hz), 3.08 (2H, qd, J=3.8, 12.0 Hz), 3.46 (2H, d, J=12.0 Hz), 3.75 (1H, tt, J=3.2, 12.0 Hz), 4.57 (2H, t, J=7.6 Hz), 7.11 (2H, d, J=7.2 Hz), 7.15 (1H, s), 7.15-7.30 (3H, m), 7.54 (1H, s), 9.57 (1H, broad s).
$^{13}$C-NMR (100 MHz, DMSO-d6), δ: 25.2 (2×CH$_2$), 36.6 (CH$_2$), 40.9 (CH), 42.6 (CH$_3$), 49.0 (CH$_2$), 52.5 (2×CH$_2$), 126.5 (CH), 127.6 (CH) 128.2 (CH), 128.4 (2×CH), 128.7 (2×CH), 128.8 (C), 137.6 (C), 140.1 (C), 191.6 (C=O).

Example 3

Preparation of 6,11-dihydro-11-(1-methyl-4-piperidinylidene)-5H-imidazo[2,1-b][3]-benzazepine as the fumarate salt (Intermediate 7)

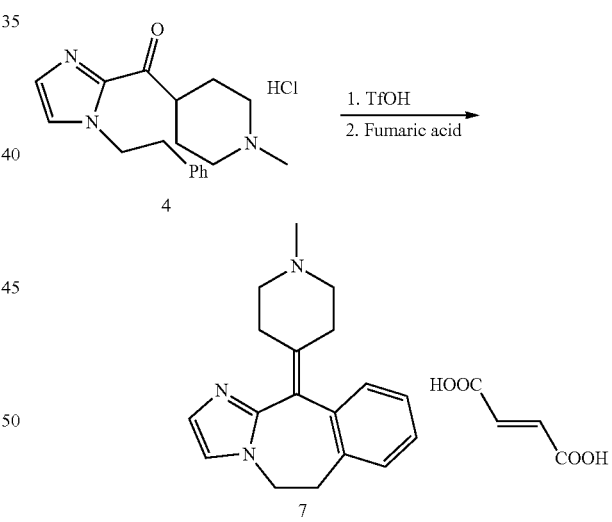

A mixture of trifluoromethanesulfonic acid (600 ml) and intermediate 4.HCl (74 g of hydrochloride salt, 0.22 mol) was heated to 95° C. for 6 hours. When the reaction was complete, the solution was cooled to 25° C. and poured into 1.5 L of cold (0/5° C.) water. The pH was adjusted to 9/10 by addition of 50% aqueous NaOH and the product was extracted with dichloromethane.

The solvent was distilled and changed to acetone and the volume was adjusted to 590 ml. Fumaric acid (25.7 g, 0.22 mol) was added and the mixture warmed to 50/55° C. for 1 hour. The solvent was distilled to a final volume of 295 ml. The suspension was cooled to 20° C., filtered and washed with cold acetone. After drying 60.5 g (69% yield) of 6,11-dihydro-11-(1-methyl-4-piperidinylidene)-5H-imidazo[2,1-b][3]-benzazepine (intermediate 7, fumarate salt) were obtained.

Spectroscopic Data of Intermediate 7 (Fumarate Salt):

$^1$H-NMR (400 MHz, DMSO-d6), δ: 2.25-2.35 (1H, m), 2.49 (3H, s, CH$_3$), 2.45-2.55 (1H, m), 2.67 (1H, t, J=8.4 Hz), 2.75-2.85 (1H, m), 2.85-3.10 (5H, m), 3.39 (1H, td, J=3.6, 14.0 Hz), 3.91 (1H, t, J=12.8 Hz), 4.36 (1H, d, J=12.8 Hz), 6.53 (2H, s, 2×CH fumaric acid), 6.90 (1H, s), 7.02 (1H, s), 7.09 (1H, d, J=6.8 Hz), 7.23 (2H, quint, J=7.2 Hz), 7.34 (1H, d, J=6.8 Hz), 10.4 (3H, broad s, 2×COOH+NH).

$^{13}$C-NMR (100 MHz, DMSO-d6), δ: 28.6 (CH$_2$), 28.7 (CH$_2$), 30.3 (CH$_2$), 43.1 (CH$_3$), 48.3 (CH$_2$), 54.2 (CH$_2$), 54.4 (CH$_2$), 121.2 (CH), 125.5 (C), 126.6 (CH), 127.1 (CH), 127.9 (CH), 128.4 (CH), 128.6 (CH), 134.8 (2×CH, fumaric acid), 136.8 (C), 137.1 (C), 139.1 (C), 142.6 (C), 167.6 (2×COO).

Example 4

Preparation of 6,11-dihydro-11-(1-methyl-4-piperidinylidene)-5H-imidazo[2,1-b][3]-benzazepine as the fumarate salt (intermediate 7)

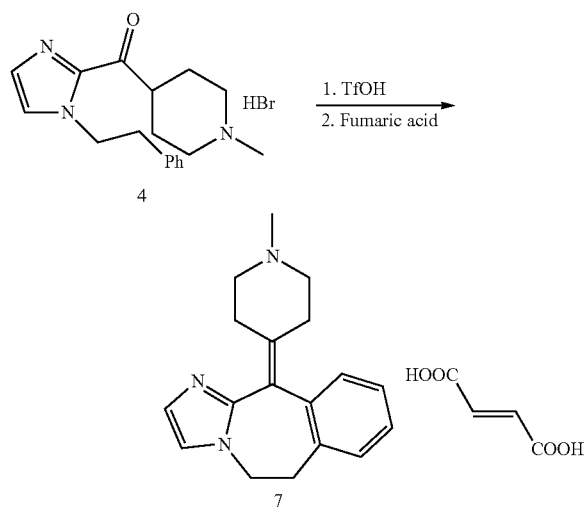

A mixture of trifluoromethanesulfonic acid (150 ml) and intermediate 4.HBr (14.5 g of hydrobromide salt, 0.04 mol) was heated to 105° C. for 6 hours. When the reaction was complete the solution was cooled to 25° C. and poured into water (450 ml) at 0/5° C. The pH was adjusted to 9/10 by addition of 50% aqueous NaOH and the product was extracted with dichloromethane.

The solvent was distilled and changed to acetone and the volume was adjusted to 110 ml. Fumaric acid (4.4 g, 0.04 mol) was added and the mixture warmed to 50/55° C. for 1 hour. The suspension was cooled to 0° C., filtered and washed with cold acetone. After drying 9.9 g (65% yield) of 6,11-dihydro-11-(1-methyl-4-piperidinylidene)-5H-imidazo[2,1-b][3]-benzazepine (intermediate 7, fumarate salt) were obtained.

Example 5

Preparation of 6,11-dihydro-11-(1-methyl-4-piperidinylidene)-5H-imidazo[2,1-b][3]-benzazepine as the fumarate salt (intermediate 7)

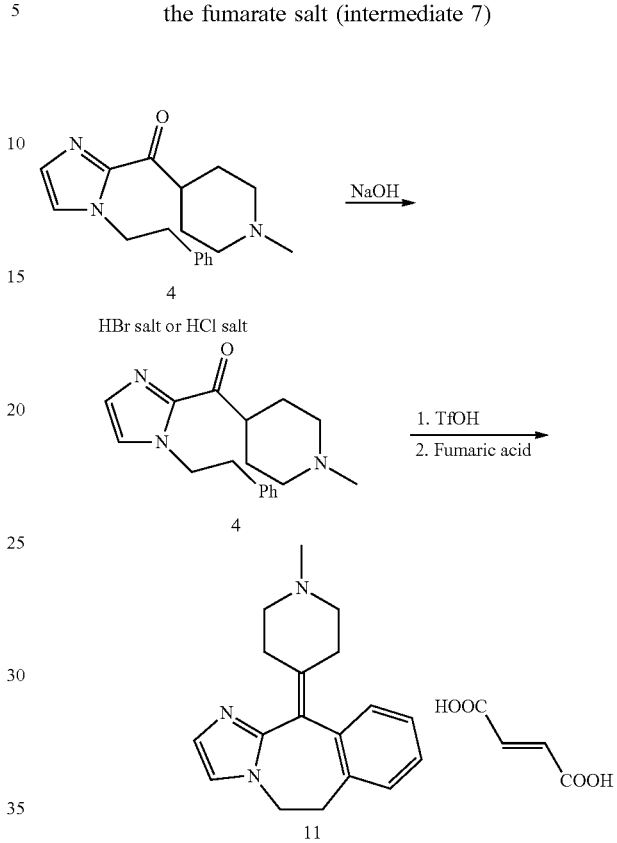

Intermediate 4 (3.53 g of hydrochloride salt or 4.0 g of hydrobromide salt, 0.011 mol) was dissolved in water (20 ml) and dichloromethane (20 ml). The pH was adjusted to 9-10 by addition of 50% aqueous NaOH and the product was extracted with dichloromethane.

The solvent was distilled off and to the resulting oil, trifluoromethanesulfonic acid (30 ml) was added and the reaction heated to 105° C. for 6 hours. The solution was cooled to 25° C. and poured into into water (30 ml) at 0/5° C. The pH was adjusted to 9/10 by addition of 50% aqueous NaOH and the product was extracted with dichloromethane.

The solvent was distilled off and changed to acetone and the volume was adjusted to 110 ml. Fumaric acid (1.2 g, 0.011 mol) was added and the mixture warmed to 50/55° C. for 1 hour. The suspension was cooled to 0° C., filtered and washed with cold acetone. After drying 2.5 g (58% yield) of 6,11-dihydro-11-(1-methyl-4-piperidinylidene)-5H-imidazo[2,1-b][3]-benzazepine (intermediate 7, fumarate salt) were obtained.

Intermediate 7 was also isolated, after reaction according to the previous examples, as:
Free base: The final organic phase was distilled off and the solvent changed to ethyl acetate/heptanes. The product was isolated by filtration.

Spectroscopic Data of Intermediate 7 (Free Base):

$^1$H-NMR (400 MHz, DMSO-d6), δ: 1.98 (1H, td, J=3.2, 9.6 Hz), 2.05-2.20 (2H, m), 2.11 (3H, s, CH$_3$), 2.29 (1H, ddd, J=5.2, 9.2, 13.6 Hz), 2.45-2.55 (1H, m), 2.55-2.75 (3H, m), 2.92 (1H, dt, J=3.2, 13.6 Hz), 3.33 (1H, td, J=4.0, 13.6

Hz), 3.89 (1H, td, J=3.2, 13.6 Hz), 4.35 (1H, dt, J=4.0, 13.6 Hz), 6.85 (1H, s), 6.97 (1H, s), 7.05 (1H, d, J=6.8 Hz), 7.15-7.25 (2H, m), 7.32 (1H, d, J=6.8 Hz).

$^{13}$C-NMR (100 MHz, DMSO-d6), δ: 30.4 (CH$_2$), 30.7 (CH$_2$), 30.8 (CH$_2$), 45.6 (CH$_3$), 48.2 (CH$_2$), 56.4 (CH$_2$), 56.5 (CH$_2$), 120.8 (CH), 124.0 (C), 126.4 (CH), 127.0 (CH), 127.5 (CH), 128.4 (CH), 128.5 (CH), 137.0 (C), 139.7 (C), 140.5 (C), 143.1 (C).

Succinate salt: The final organic phase was distilled off and the solvent changed to acetone or ethyl acetate. Succinic acid (1 mol eq.) was added, the suspension was stirred and the product isolated by filtration.

Spectroscopic Data of Intermediate 7 (Succinate Salt):

$^1$H-NMR (400 MHz, DMSO-d6), δ: 2.15-2.25 (1H, m), 2.30 (3H, s, CH$_3$), 2.25-2.45 (3H, m), 2.37 (4H, s, succinic acid), 2.70-2.85 (4H, m), 2.93 (1H, d, J=14.0 Hz), 3.36 (1H, td, J=4.0, 14.0 Hz), 3.90 (1H, td, J=2.8, 12.8 Hz), 4.36 (1H, d, J=12.0 Hz), 6.53 (2H, s, 2×CH fumaric acid), 6.89 (1H, s), 7.00 (1H, s), 7.07 (1H, d, J=6.4 Hz), 7.15-7.25 (2H, m), 7.33 (1H, d, J=6.4 Hz), 9.1 (3H, broad s, 2×COOH+NH).

$^{13}$C-NMR (100 MHz, DMSO-d6), δ: 29.5 (CH$_2$), 29.6 (2×CH$_2$, succinic acid), 29.7 (CH$_2$), 30.4 (CH$_2$), 44.4 (CH$_3$), 48.3 (CH$_2$), 55.3 (CH$_2$), 55.5 (CH$_2$), 121.1 (CH), 124.7 (C), 126.6 (CH), 127.0 (CH), 127.7 (CH), 128.5 (CH), 128.6 (CH), 137.1 (C), 138.6 (C), 139.4 (C), 142.8 (C), 174.2 (2×COO).

Maleate salt: The final organic phase was distilled off and the solvent changed to acetone. Maleic acid (1 mol eq.) was added, the suspension was stirred and the product isolated by filtration.

Spectroscopic Data of Intermediate 7 (Maleate Salt):

$^1$H-NMR (400 MHz, DMSO-d6), δ: 2.35-2.60 (2H, m), 2.47 (3H, s, CH$_3$), 2.77 (2H, 2), 3.01 (1H, d, J=14.0 Hz), 3.25-3.55 (4H, m), 4.02 (1H, td, J=3.2, 12.8 Hz), 4.45 (1H, d, J=13.2 Hz), 6.07 (2H, s, 2×CH maleic acid), 7.14 (1H, d, J=6.8 Hz), 7.26 (1H, s), 7.28 (1H, s), 7.25-7.35 (2H, m), 7.40 (1H, d, J=6.8 Hz).

$^{13}$C-NMR (100 MHz, DMSO-d6), δ: 27.7 (CH$_2$), 27.9 (CH$_2$), 30.0 (CH$_2$), 42.3 (CH$_3$), 48.8 (CH$_2$), 53.2 (CH$_2$), 53.5 (CH$_2$), 122.5 (CH), 127.0 (C), 128.3 (CH), 128.6 (CH), 128.9 (CH), 134.5 (2×CH, maleic acid), 137.0 (C), 138.4 (C), 139.7 (C), 141.9 (C), 167.1 (2×COO).

Tartrate salt: The final organic phase was distilled off and the solvent changed to acetone. Tartaric acid (1 mol eq.) was added, the suspension was stirred and the product isolated by filtration.

Spectroscopic Data of Intermediate 7 (Tartrate Salt):

$^1$H-NMR (400 MHz, DMSO-d6), δ: 2.25-2.35 (1H, m), 2.47 (3H, s, CH$_3$), 2.50-2.60 (1H, m), 2.64 (2H, s), 2.80-3.05 (3H, m), 3.10-3.20 (2H, m), 3.41 (1H, td, J=3.6, 14.0 Hz), 3.92 (1H, td, J=3.2, 12.8 Hz), 4.19 (2H, s, tartaric acid), 4.37 (1H, d, J=12.8 Hz), 6.82 (5H, broad s, 2×COOH+2×OH+NH), 6.92 (1H, s), 7.05 (1H, s), 7.10 (1H, d, J=7.2 Hz), 7.24 (2H, quint, J=7.2 Hz), 7.35 (1H, d, J=7.2 Hz).

$^{13}$C-NMR (100 MHz, DMSO-d6), δ: 28.0 (CH$_2$), 30.3 (CH$_2$), 30.8 (CH$_2$), 42.6 (CH$_3$), 48.4 (CH$_2$), 53.8 (CH$_2$), 54.0 (CH$_2$), 72.2 (2×CH, tartaric acid), 121.5 (CH), 125.8 (C), 126.8 (CH), 126.9 (CH), 128.1 (CH), 128.4 (CH), 128.7 (CH), 135.7 (C), 137.8 (C), 138.9 (C), 142.4 (C), 173.9 (2×COO).

Example 6

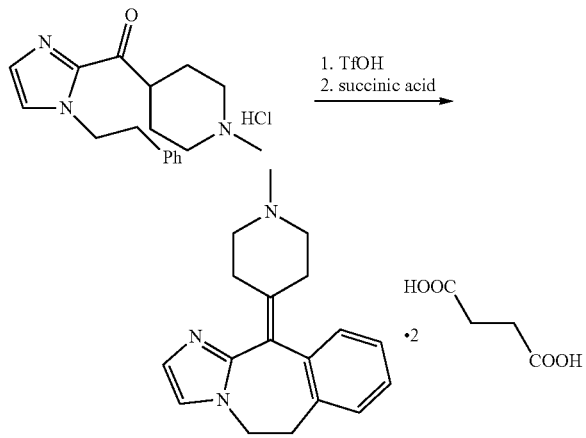

A mixture of trifluoromethanesulfonic acid (160 ml) and intermediate 4.HCl (20 g of hydrochloride salt, 0.06 mol) was heated to 95° C. for 6 hours. When the reaction was complete, the solution was cooled to 25° C. and poured into 400 ml of cold (0/5° C.) water. The pH was adjusted to 9/10 by addition of 50% aqueous NaOH and the product was extracted with dichloromethane.

The solvent was distilled and changed to acetone and the volume was adjusted to 60 ml. Succinic acid (17.0 g, 0.14 mol) was added and the mixture warmed to 50/55° C. for 1 hour. The suspension was cooled to 0° C., filtered and washed with cold acetone. After drying 22.0 g (71% yield) of 6,11-dihydro-11-(1-methyl-4-piperidinylidene)-5H imidazo[2,1-b][3]-benzazepine (intermediate 7, succinate salt) were obtained.

Example 7

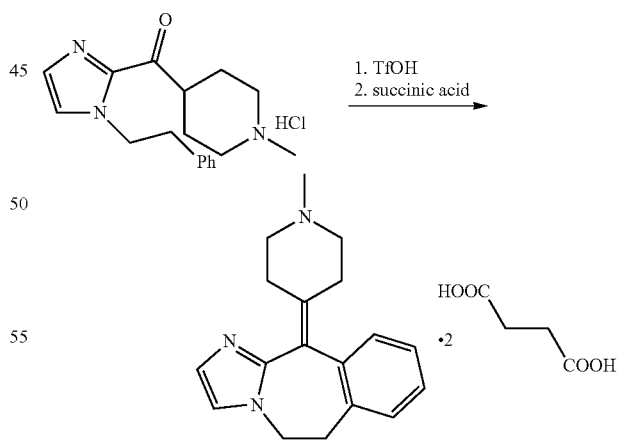

A mixture of trifluoromethanesulfonic acid (80 ml) and intermediate 4.HCl (10 g of hydrochloride salt, 0.03 mol) was heated to 95° C. for 6 hours. When the reaction was complete, the solution was cooled to 25° C. and poured into 200 ml of cold (0/5° C.) water. The pH was adjusted to 9/10 by addition of 50% aqueous NaOH and the product was extracted with dichloromethane.

The solvent was distilled and changed to acetone and the volume was adjusted to 60 ml. Isopropanol (7 ml) and succinic acid (8.5 g, 0.07 mol) were added and the mixture warmed to 50/55° C. for 1 hour. The suspension was cooled to 0° C., filtered and washed with cold acetone. After drying 9.5 g (61% yield) of 6,11-dihydro-11-(1-methyl-4-piperidinylidene)-5H imidazo[2,1-b][3]-benzazepine (intermediate 7, succinate salt) were obtained.

Example 8

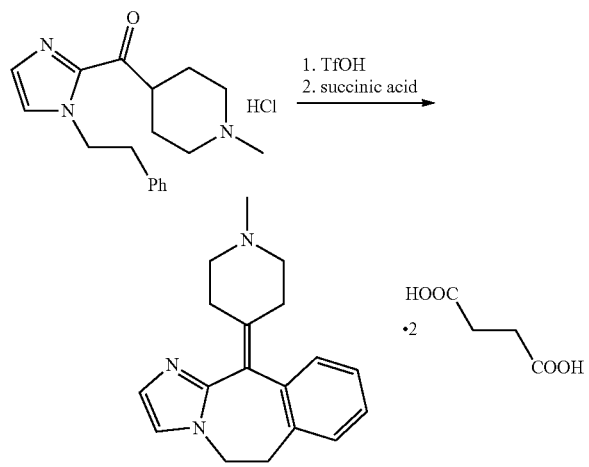

A mixture of trifluoromethanesulfonic acid (40 ml) and intermediate 4.HCl (5.0 g of hydrochloride salt, 0.015 mol) was heated to 95° C. for 6 hours. When the reaction was complete, the solution was cooled to 25° C. and poured into 100 ml of cold (0/5° C.) water. The pH was adjusted to 9/10 by addition of 50% aqueous NaOH and the product was extracted with dichloromethane.

The solvent was distilled and changed to acetone and the volume was adjusted to 60 ml. Methanol (2.5 ml) and succinic acid (4.3 g, 0.036 mol) were added and the mixture warmed to 50/55° C. for 1 hour. The suspension was cooled to 0° C., filtered and washed with cold acetone. After drying 3.2 g (41% yield) of 6,11-dihydro-11-(1-methyl-4-piperidinylidene)-5H imidazo[2,1-b][3]-benzazepine (intermediate 7, succinate salt) were obtained.

Example 9

Preparation of 6,11-dihydro-3-hydroxymethyl-11-(1-methyl-4-piperidinylidene)-5H-imidazo[2,1-b][3]-benzazepine as the fumarate salt in the presence of sodium acetate (Intermediate 11.fumarate)

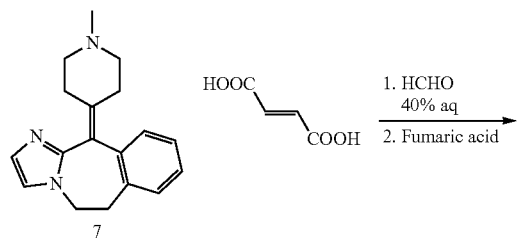

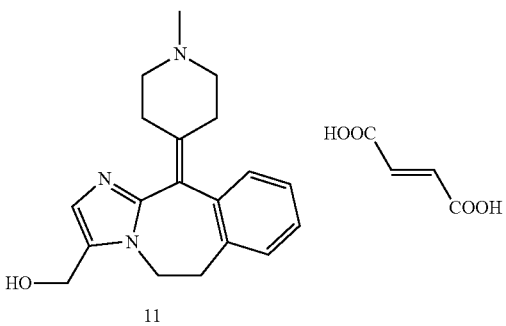

A mixture of intermediate 7 (5.0 g of the fumarate salt, 0.013 mol), 40% aqueous formaldehyde (22.5 ml) and sodium acetate (1.5 g, 0.02 mol) was heated to 95° C. for 20 hours. After this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 70%), intermediate 7 (ca 15%) and 2,3-dihydroxymethyl impurity: 6,11-dihydro-2,3-dihydroxymethyl-11-(1-methyl-4-piperidinylidene)-5H-imidazo[2,1-b][3]-benzazepine (ca 15%).

The reaction was cooled to 20° C., the pH was adjusted to 9-10 by addition of 50% aqueous NaOH and the product was extracted with dichloromethane.

The solvent was distilled and changed to acetone to a final volume of 40 ml. Fumaric acid (1.5 g, 0.013 mol) was added and the mixture heated to reflux for 1 hour. The suspension was cooled to 0° C., filtered and washed to afford a solid (4.7 g 85% yield) consisting of a mixture of 6,11-dihydro-3-hydroxymethyl-11-(1-methyl-4-piperidinylidene)-5H-imidazo[2,1-b][3]-benzazepine (intermediate 11) (ca 70%), intermediate 7 (ca 15%) and the 2,3-dihydroxymethyl impurity: 6,11-dihydro-2,3-dihydroxymethyl-11-(1-methyl-4-piperidinylidene)-5H-imidazo[2,1-b][3]-benzazepine (ca 15%).

Example 10

Preparation of 6,11-dihydro-3-hydroxymethyl-11-(1-methyl-4-piperidinylidene)-5H-imidazo[2,1-b][3]-benzazepine as the fumarate salt in the presence of sodium acetate (Intermediate 11.fumarate)

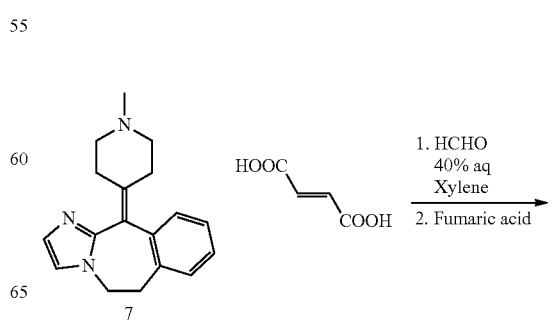

19

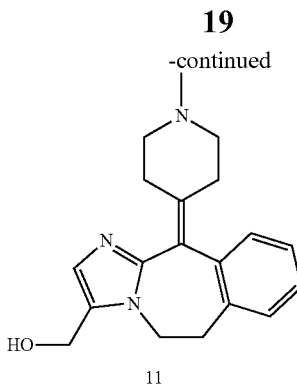 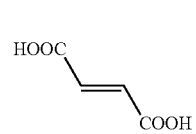

11

A mixture of intermediate 7 (138 g of the fumarate salt, 0.32 mol), xylene (270 ml) 40% aqueous formaldehyde (540 ml) and sodium acetate trihydrate (59.5 g) was heated to 95° C. for 20 hours. After this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 70%), intermediate 7 (ca 15%) and the 2,3-dihydroxymethyl impurity (ca 15%).

The reaction was cooled to 20° C., and the two phases were separated. The pH of the aqueous phase containing the product was adjusted to 9-10 by addition of 50% aqueous NaOH and the product was extracted with dichloromethane. The solvent was distilled and changed to acetone to a final volume of 550 ml. Fumaric acid (41.4 g, 0.36 mol) was added and the mixture heated to reflux for 1 hour. The suspension was cooled to 0° C., filtered and washed to afford 98.1 g (71% yield) of a solid consisting of a mixture of 6,11-dihydro-3-hydroxymethyl-11-(1-methyl-4-piperidinylidene)-5H-imidazo[2,1-b][3]-benzazepine (intermediate 11) (ca 70%), intermediate 7 (ca 18%) and the 2,3-dihydroxymethyl impurity (ca 12%).

Example 11

Preparation of 6,11-dihydro-3-hydroxymethyl-11-(1-methyl-4-piperidinylidene)-5H-imidazo[2,1-b][3]-benzazepine as the fumarate salt in the presence of sodium bicarbonate The reaction was carried out under the same conditions as disclosed in example 10, but using NaHCO₃ instead of sodium acetate.

The mixture was heated to 95° C. for 40 hours, after this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 62%), intermediate 7 (ca 32%) and the 2,3-dihydroxymethyl impurity (ca 5%).

Example 12

Preparation of 6,11-dihydro-3-hydroxymethyl-11-(1-methyl-4-piperidinylidene)-5H-imidazo[2,1-b][3]-benzazepine (intermediate 11) as the fumarate salt in the presence of sodium bicarbonate

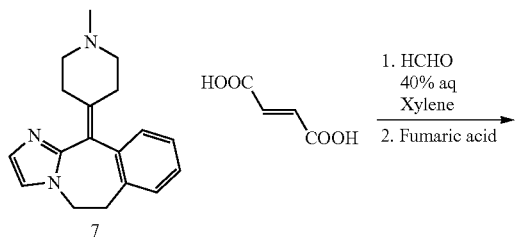

7

20

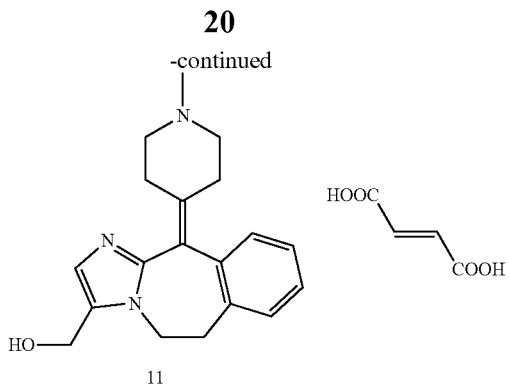

11

A mixture of intermediate 7 (2 g of the fumarate salt, 0.0049 mol), xylene (4 ml) 40% aqueous formaldehyde (8 ml) and sodium bicarbonate (0.6 g) was heated to 95° C. for several hours. The relation of starting material (intermediate 7), final product (intermediate 11) and the 2,3-dihydroxymethyl impurity was monitored from time to time giving rise to the following results:

| Time (Hours) | % intermediate 7 | % intermediate 11 | % 2,3-dihydroxy methyl impurity |
| --- | --- | --- | --- |
| 17 | 61.01 | 37.72 | 1.27 |
| 24 | 51.43 | 46.67 | 2.1 |
| 40 | 38.66 | 57.39 | 3.95 |
| 47 | 32.5 | 62.68 | 4.82 |
| 68 | 27.74 | 65.61 | 6.66 |

Example 13

Preparation of 6,11-dihydro-3-hydroxymethyl-11-(1-methyl-4-piperidinylidene)-5H-imidazo[2,1-b][3]-benzazepine (intermediate 11) as the fumarate salt in the presence of pyridine

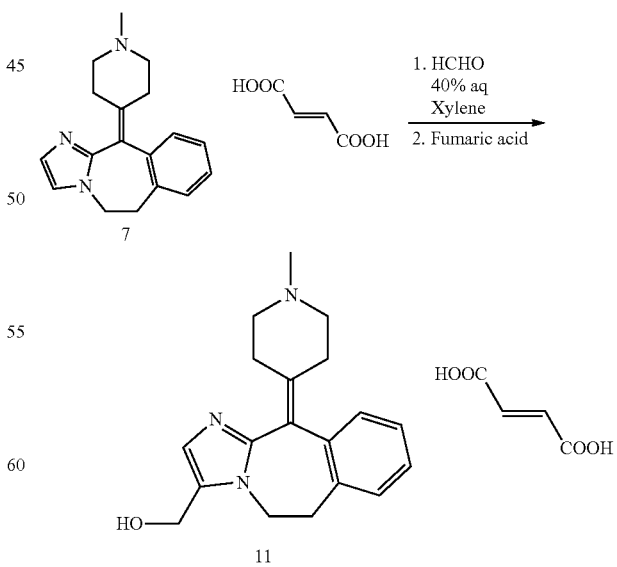

A mixture of intermediate 7 (2 g of the fumarate salt, 0.0049 mol), xylene (4 ml) 40% aqueous formaldehyde (8 ml) and pyridine (0.46 g) was heated to 95° C. for several hours. The relation of starting material (intermediate 7), final product (intermediate 11) and the 2,3-dihydroxymethyl impurity was monitored from time to time giving rise to the following results:

| Time (Hours) | % intermediate 7 | % intermediate 11 | % 2,3-dihydroxy methyl impurity |
|---|---|---|---|
| 17 | 43.67 | 52.66 | 3.67 |
| 24 | 31.91 | 62.22 | 5.87 |
| 40 | 16.64 | 71.39 | 11.97 |
| 47 | 12.28 | 69.22 | 18.5 |
| 68 | 10.76 | 64.97 | 24.27 |

Example 14

Preparation of 6,11-dihydro-3-hydroxymethyl-11-(1-methyl-4-piperidinylidene)-5H-imidazo[2,1-b][3]-benzazepine (intermediate 11) from intermediate 7 as the maleate salt

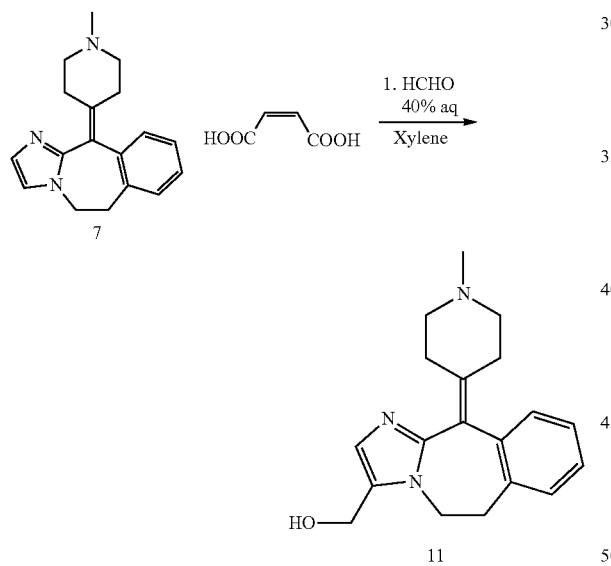

A mixture of intermediate 7 (2.2 g as the maleate salt, 0.0056 mol), xylene (4 ml) 40% aqueous formaldehyde (8 ml) and sodium acetate trihydrate (0.91 g) was heated to 95° C. for several hours. The relation of starting material (intermediate 7), final product (intermediate 11) and the 2,3-dihydroxymethyl impurity was monitored from time to time giving rise to the following results:

| Time (Hours) | % intermediate 7 | % intermediate 11 | % 2,3-dihydroxy methyl impurity |
|---|---|---|---|
| 4.5 | 91.13 | 8.77 | 0.09 |
| 20.5 | 61.97 | 36.56 | 1.47 |
| 26.5 | 50.88 | 46.71 | 2.4 |
| 44 | 35.58 | 59.12 | 5.3 |

Example 15

Preparation of 6,11-dihydro-3-hydroxymethyl-11-(1-methyl-4-piperidinylidene)-5H-imidazo[2,1-b][3]-benzazepine (intermediate 11) from intermediate 7 as the succinate salt

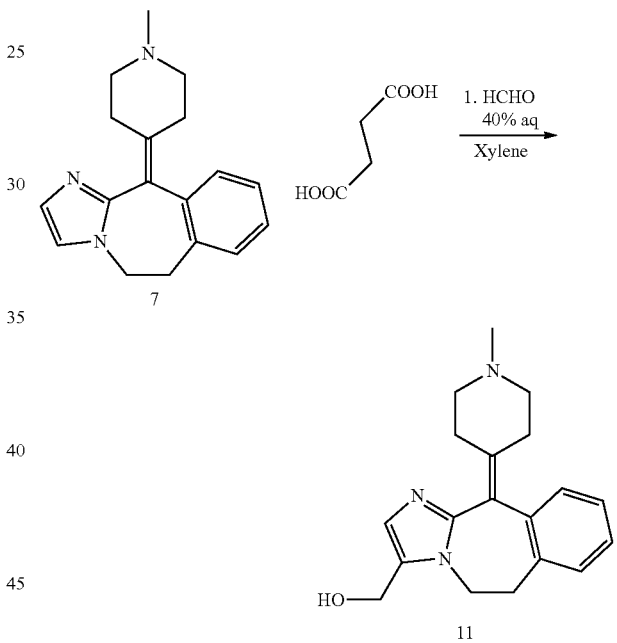

A mixture of intermediate 7 (2.2 g as the succinate salt, 0.0056 mol), xylene (4 ml) 40% aqueous formaldehyde (8 ml) and sodium acetate trihydrate (0.91 g) was heated to 95° C. for several hours. The relation of starting material (intermediate 7), final product (intermediate 11) and the 2,3-dihydroxymethyl impurity was monitored from time to time giving rise to the following results:

| Time (Hours) | % intermediate 7 | % intermediate 11 | % 2,3-dihydroxy methyl impurity |
|---|---|---|---|
| 4.5 | 73.65 | 25.73 | 0.62 |
| 20.5 | 18.02 | 74.65 | 7.32 |
| 26.5 | 11.03 | 77.94 | 11.03 |
| 44 | 3.78 | 77.35 | 18.23 |

Example 16

Preparation of 6,11-dihydro-3-hydroxymethyl-11-(1-methyl-4-piperidinylidene)-5H-imidazo[2,1-b][3]-benzazepine (intermediate 11) from intermediate 7 as the (+)-tartrate salt

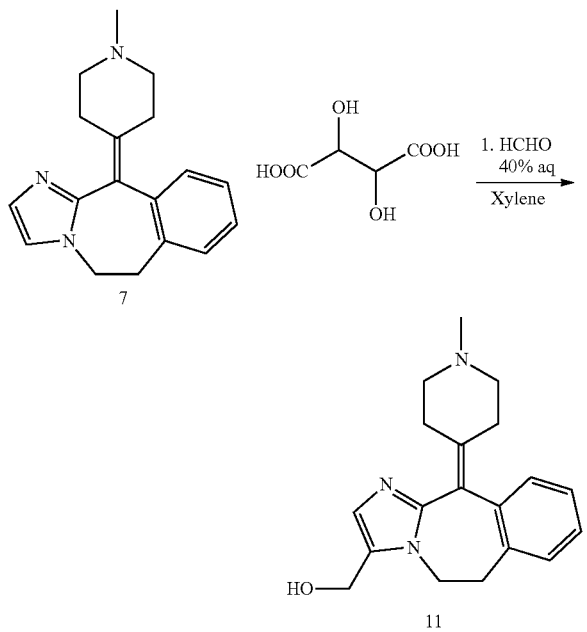

A mixture of intermediate 7 (2.4 g as the tartrate salt, 0.0056 mol), xylene (4 ml) 40% aqueous formaldehyde (8 ml) and sodium acetate trihydrate (0.91 g) was heated to 95° C. for several hours. The relation of starting material (intermediate 7), final product (intermediate 11) and the 2,3-dihydroxymethyl impurity was monitored from time to time giving rise to the following results:

| Time (Hours) | % intermediate 7 | % intermediate 11 | % 2,3-dihydroxy methyl impurity |
|---|---|---|---|
| 4.5 | 89.06 | 10.68 | 0.27 |
| 20.5 | 54.26 | 42.61 | 3.12 |
| 26.5 | 42.75 | 52.2 | 5.05 |
| 44 | 28.26 | 63.23 | 8.51 |

Example 17

Preparation of 6,11-dihydro-3-hydroxymethyl-11-(1-methyl-4-piperidinylidene)-5H-imidazo[2,1-b][3]-benzazepine (intermediate 11) as the fumarate salt without the presence of a base The reaction was carried out under the same conditions as disclosed in example 10, but without addition of any base.

The mixture was heated to 95° C. for 32 hours, after this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 42%), intermediate 7 (ca 50%) and the 2,3-dihydroxymethyl impurity (ca 8%).

Example 18

Preparation of 6,11-dihydro-3-hydroxymethyl-11-(1-methyl-4-piperidinylidene)-5H-imidazo[2,1-b][3]-benzazepine (intermediate 11) as the fumarate salt in the presence of pyridine The reaction was carried out under the same conditions as disclosed in example 10, but using pyridine instead of sodium acetate.

The mixture was heated to 95° C. for 32 hours, after this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 68%), intermediate 7 (ca 20%) and the 2,3-dihydroxymethyl impurity (ca 5%).

Example 19

Preparation of 6,11-dihydro-3-hydroxymethyl-11-(1-methyl-4-piperidinylidene)-5H-imidazo[2,1-b][3]-benzazepine (intermediate 11) as the fumarate salt in the presence of Triton B The reaction was carried out under the same conditions as disclosed in example 10, but using Triton B instead of sodium acetate.

The mixture was heated to 95° C. for 32 hours, after this time a HPLC analysis showed a mixture of 6,11-dihydro-3-hydroxymethyl-11-(1-methyl-4-piperidinylidene)-5H-imidazo[2,1-b][3]-benzazepine (intermediate 11) (ca 48%), intermediate 7 (ca 48%) and the 2,3-dihydroxymethyl impurity (ca 4%).

Example 20

Comparative Example

Preparation of 6,11-dihydro-3-hydroxymethyl-11-(1-methyl-4-piperidinylidene)-5H-imidazo[2,1-b][3]-benzazepine (Intermediate 11) following the methodology described in the prior art: EP 0 588 858

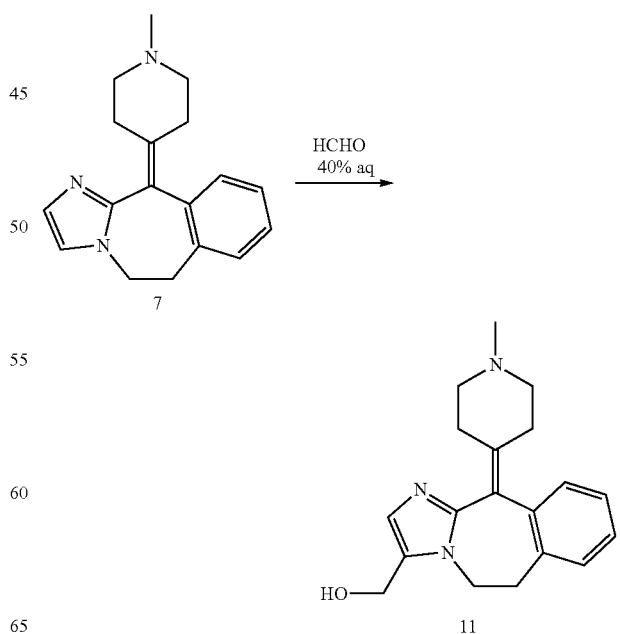

A mixture of intermediate 7 as the free base (5 g) and 40% aqueous formaldehyde was heated to reflux for 1 week. After this time a HPLC analysis showed a mixture of the starting material (intermediate 7—free base) and final product (intermediate 11) in a 50% ratio.

The reaction was cooled to 20° C., the pH was adjusted to 9-10 by addition of 50% aqueous NaOH and the product was extracted with dichloromethane.

The solvent was distilled off and the oil residue was purified by flash chromatography to obtain 1 g of 6,11-dihydro-3-hydroxymethyl-11-(1-methyl-4-piperidinylidene)-5H-imidazo[2,1-b][3]-benzazepine (intermediate 11) as the free base.

Spectroscopic Data of Intermediate 11 (Free Base):
$^1$H-NMR (400 MHz, DMSO-d6), δ: (1.95-2.05, 1H, m), 2.05-2.20 (1H, m), 2.13 (3H, s, CH$_3$), 2.25-2.35 (1H, m), 2.45-2.55 (1H, m), 2.55-2.65 (1H, m), 2.65-2.70 (1H, m), 2.70-2.80 (1H, m). 2.98 (1H, d, J=14.0 Hz), 3.37 (1H, dt, J=4.0, 14.0 Hz), 3.89 (1H, dt, J=4.0, 14.0 Hz), 4.30-4.40 (1H, m), 4.36 (2H, s), 4.90 (1H, broad s, OH), 6.77 (1H, s), 7.05 (1H, d, J=6.4 Hz), 7.15-7.25 (2H, m), 7.33 (1H, s, J=6.4 Hz).

$^{13}$C-NMR (100 MHz, DMSO-d6), δ: 30.0 (CH$_2$), 30.6 (CH$_2$), 30.7 (CH$_2$), 45.5 (CH$_3$), 46.0 (CH$_2$), 52.9 (CH$_2$), 56.2 (CH$_2$), 56.4 (CH$_2$), 124.2 (C), 125.8 (CH), 126.3 (CH), 127.4 (CH), 128.1 (CH), 128.2 (CH), 132.0 (C), 136.9 (C), 139.7 (C), 140.2 (C), 143.7 (C).

Example 21

Preparation of 6,11-dihydro-11-(1-methyl-4-piperidinylidene)-5H-imidazo[2,1-b][3]-benzazepine-3-carboxaldehyde (Alcaftadine)

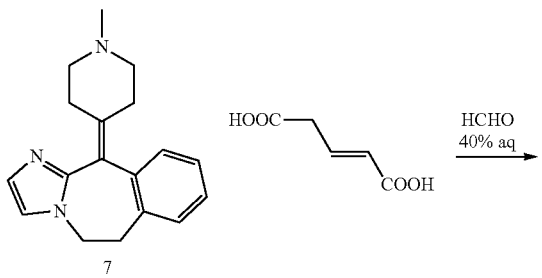

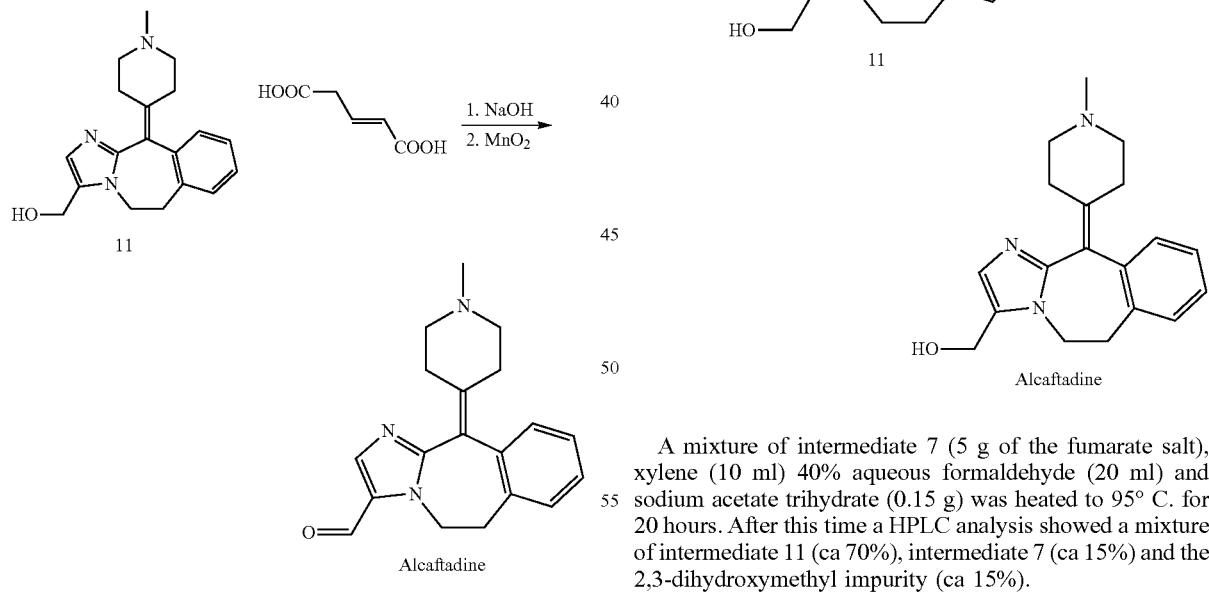

Intermediate 11 (88.4 g of the fumarate salt) was dissolved in dichloromethane (440 ml) and water (440 ml) and the pH was adjusted to 9-10 by addition of 50% aqueous NaOH and the product was extracted with dichloromethane.

The organic phase was distilled and the solvent was changed to toluene to a final volume of 440 ml. Manganese (IV) oxide (440 g) was added and the reaction was heated to 60° C. for 2 hours.

The reaction mixture was cooled down to 20° C. The solids were filtered off and washed with toluene (880 ml). The filtered liquids were concentrated to a final volume of 150 ml and diisopropyl ether (880 ml) was added. The solid was filtered and washed with diisopropylether. Crude Alcaftadine (49.5 g, 85%) was obtained with 90% purity.

Example 22

Preparation of 6,11-dihydro-11-(1-methyl-4-piperidinylidene)-5H-imidazo[2,1-b][3]-benzazepine-3-carboxaldehyde (Alcaftadine) in a One-Pot process from intermediate 7 as the fumarate salt

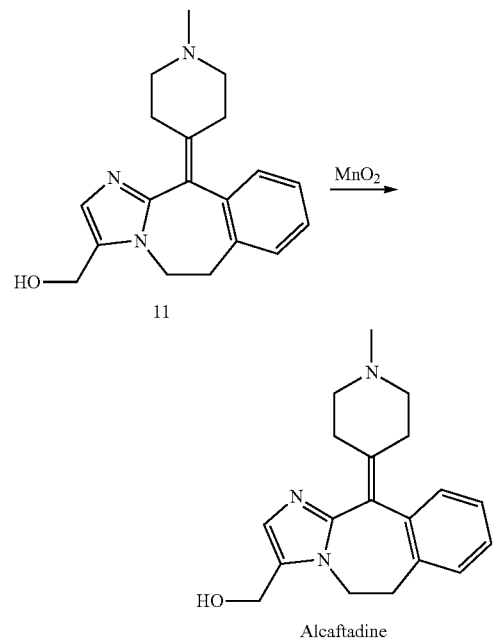

A mixture of intermediate 7 (5 g of the fumarate salt), xylene (10 ml) 40% aqueous formaldehyde (20 ml) and sodium acetate trihydrate (0.15 g) was heated to 95° C. for 20 hours. After this time a HPLC analysis showed a mixture of intermediate 11 (ca 70%), intermediate 7 (ca 15%) and the 2,3-dihydroxymethyl impurity (ca 15%).

The reaction was cooled to 20° C., and the two phases were separated. The pH of the aqueous phase containing the product was adjusted to 9-10 by addition of 50% aqueous NaOH and the product was extracted with dichloromethane.

The organic phase was concentrated to a final volume of 25 ml, manganese (IV) oxide (25 g) was added and the suspension was refluxed for 2 hours.

The reaction mixture was cooled down to 20° C. The solids were filtered off and washed with dichloromethane (50 ml). The filtered liquids were concentrated to a final volume of 15 ml and diisopropyl ether (100 ml) was added. The solid was filtered and washed with diisopropylether. Crude Alcaftadine (2.4 g) was obtained with >90% purity.

Example 23

Preparation of 6,11-dihydro-11-(1-methyl-4-piperidinylidene)-5 5H-imidazo[2,1-b][3]-benzazepine-3-carboxaldehyde (Alcaftadine) in a One-Pot process from intermediate 7 as the succinate salt

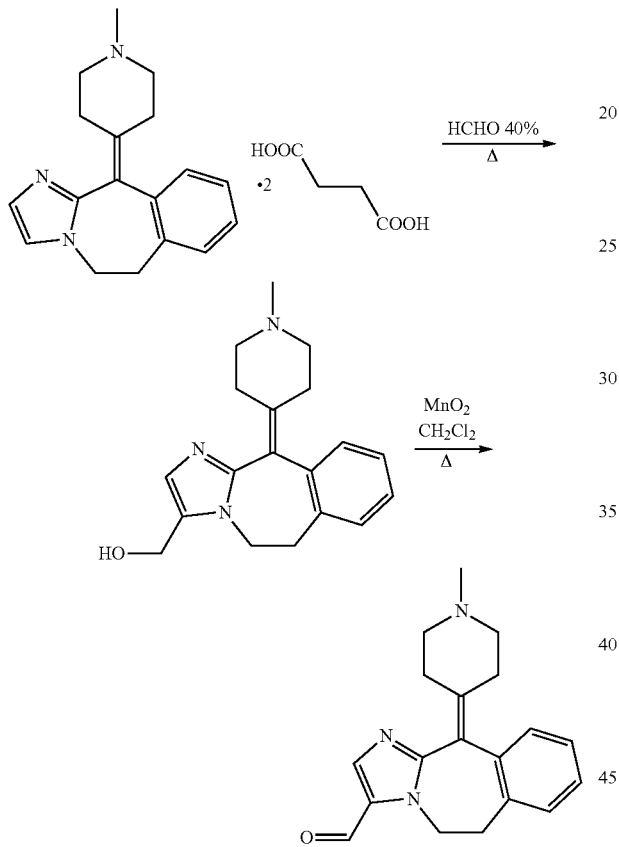

A mixture of intermediate 7 (10 g of the succinate salt) and aqueous formaldehyde (40 ml) were heated to 95° C. for 20 hours. After this time a HPLC analysis showed a mixture of intermediate 11 (ca 70%), intermediate 7 (ca 15%) and the 2,3-dihydroxymethyl impurity (ca 15%).

The reaction was cooled to 20° C. The pH was adjusted to 9-10 by addition of 50% aqueous NaOH and the product was extracted with dichloromethane. The organic phase was concentrated to a final volume of 30 ml, manganese (IV) oxide (25 g) and water (3 ml) were added and the suspension was refluxed for 2 hours.

The reaction mixture was cooled down to 20° C. The solids were filtered off and washed with dichloromethane (50 ml). The filtered liquids were concentrated to a final volume of 15 ml and diisopropyl ether (100 ml) was added. The solid was filtered and washed with diisopropylether. Crude Alcaftadine (4.7 g) was obtained with >90% purity.

Example 24

Purification of Alcaftadine

In Ethyl Acetate

Crude Alcaftadine (2.3 g) was dissolved in dichloromethane/ethyl acetate. The dichloromethane solvent was distilled and changed to ethyl acetate, to a final volume of 11 ml. The suspension was cooled to 20° C. and the solid was filtered and washed with ethyl acetate and dried. Alcaftadine (1.5 g, 65% yield) was obtained with >99% purity.

In Isopropyl Alcohol.

Crude Alcaftadine (2.5 g) was suspended in isopropyl alcohol (25 ml) and the mixture was heated to 45/50° C. until all the product was dissolved. The solvent was distilled to a final volume of 7.5 ml and the suspension obtained was cooled to 20° C. The solid was filtered, washed with isopropanol and dried. Alcaftadine (1.7 g, 68% yield) was obtained with >99% purity.

Spectroscopic Data of Alcaftadine:

$^1$H-NMR (400 MHz, DMSO-d6), δ: 2.05-2.30 (2H, m), 2.19 (3H, s, CH$_3$), 2.30-2.40 (1H, m), 2.47 (1H, s), 2.55-2.75 (4H, m), 3.03 (1H, d, J=14.0 Hz), 3.39 (1H, td, J=3.6, 14.0 Hz), 4.15 (1H, td, J=2.8, 14.0 Hz), 4.62 (1H, d, J=14.0 Hz), 7.10 (1H, d, J=7.2 Hz), 7.24 (2H, quint, J=7.2 Hz), 7.35 (1H, d, J=7.2 Hz), 7.87 (1H, s), 9.60 (1H, s, CHO).

$^{13}$C-NMR (100 MHz, DMSO-d6), δ: 30.0 (CH$_2$), 30.6 (CH$_2$), 30.7 (CH$_2$), 45.1 (CH$_3$), 49.2 (CH$_2$), 55.8 (CH$_2$), 56.0 (CH$_2$), 123.3 (C), 126.7 (CH), 128.1 (CH), 128.5 (2×CH), 131.9 (C), 136.7 (C), 138.5 (C), 142.3 (CH), 143.7 (C), 149.6 (C), 179.5 (CHO).

The invention claimed is:

1. A process for the preparation of Alcaftadine or a pharmaceutically acceptable salt thereof, comprising:
    reacting the acid addition salt of formula 7 with formaldehyde to the compound of formula 11 or a salt thereof; and
    oxidizing the compound of formula 11 or a salt thereof to Alcaftadine:

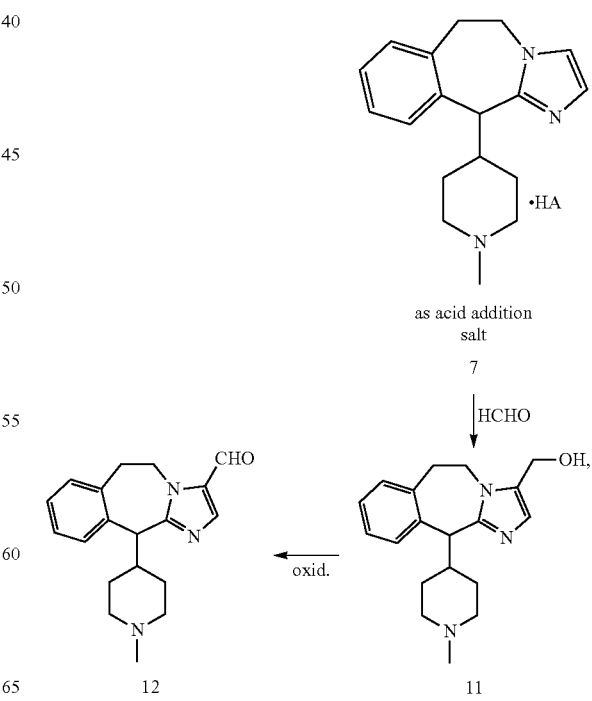

and optionally converting Alcaftadine to a pharmaceutically acceptable salt thereof,
wherein the acid addition salt of formula 7 is a salt formed with a di-carboxylic acid, EDTA, or citric acid.

2. The process according to claim 1, wherein the di-carboxylic acid is selected form the group consisting of oxalic acid, malonic acid, succinic acid, glutaric acid, adipic acid, pimelic acid, suberic acid, azelaic acid, sebacic acid, tartaric acid, fumaric acid, maleic acid, glutaconic acid, muconic acid, phthalic acid, isophthalic acid, terephthalic acid, and malic acid.

3. The process according to claim 2 wherein the di-carboxylic acid is selected from the group consisting of fumaric acid, maleic acid, succinic acid, and tartaric acid.

4. The process according to claim 3, wherein the di-carboxylic acid is fumaric acid or succinic acid.

5. The process according to claim 1, wherein the acid addition salt of formula 7 is reacted with formaldehyde in the presence of a base.

6. The process according to claim 5, wherein said base is a carboxylate, an acetate; a carbonate, a bicarbonate; an organic base, a pyridine or benzyltrimethylammonium hydroxide.

7. The process according to claim 6, wherein said base is sodium acetate, pyridine, or sodium bicarbonate.

8. The process according to claim 7, wherein said base is sodium acetate.

9. The process according to claim 1, wherein the compound of formula 11 is oxidized by reacting with manganese dioxide.

10. The process according to claim 1, wherein the acid addition salt of formula 7 is formed by reacting the compound of formula 1 with ethyl 1-methylpiperidine-4-carboxylate in the presence of a strong base to provide a compound of formula 4, which is further reacted with trifluoromethanesulfonic acid and subsequently an EDTA, a citric acid, or a di-carboxylic acid selected from the group consisting of oxalic acid, malonic acid, succinic acid, glutaric acid, adipic acid, pimelic acid, suberic acid, azelaic acid, sebacic acid, tartaric acid, fumaric acid, maleic acid, glutaconic acid, muconic acid, phthalic acid, isophthalic acid, terephthalic acid, and malic acid to provide the acid addition salt of formula 7:

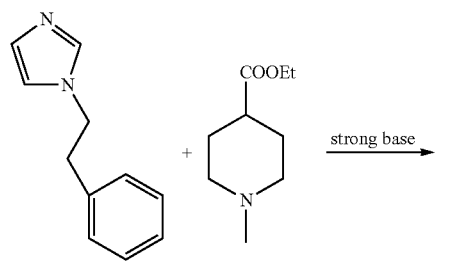

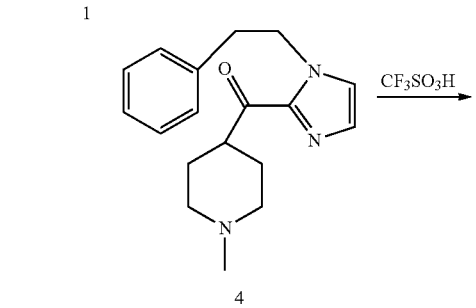

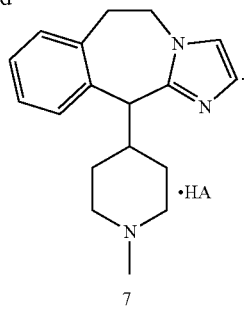

11. The process according to claim 10, wherein said strong base is lithium diisopropylamide or hexyl lithium.

12. A process for preparing Alcaftadine or a pharmaceutically acceptable salt thereof comprising reacting a compound of formula 1 with ethyl 1-methylpiperidine-4-carboxylate in the presence of a strong base to provide a compound of formula 4, which is further reacted with trifluoromethanesulfonic acid and subsequently a di-carboxylic acid, EDTA, or citric acid to provide the acid addition salt of formula 7:

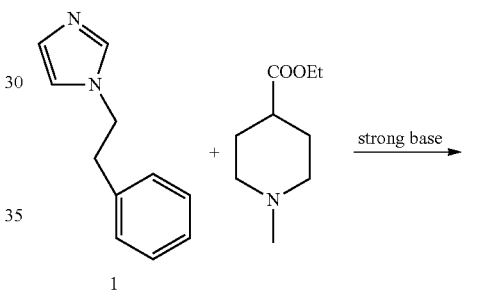

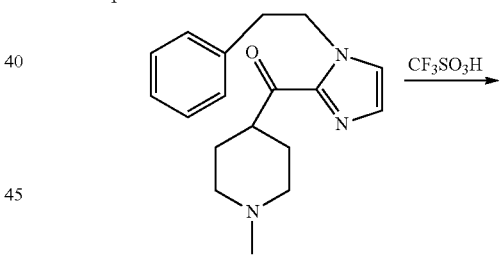

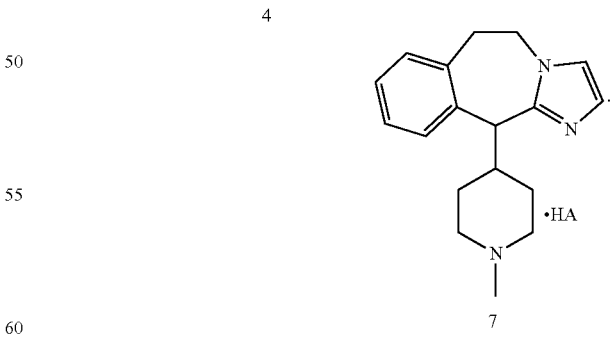

and further reacting the acid addition salt of formula 7 to provide Alcaftadine or, a pharmaceutically acceptable salt thereof.

13. The process according to claim 12, wherein said strong base is lithium diisopropylamide or hexyl lithium.

14. A process for the isolation and purification of Alcaftadine comprising crystallization in isopropyl alcohol or ethyl acetate.
15. An acid addition salt of formula 7:
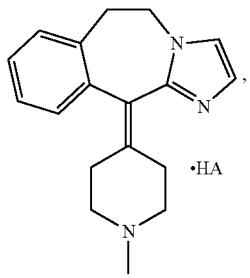
·HA
7
wherein HA is a di-carboxylic acid, EDTA, or citric acid.
* * * * *

UNITED STATES PATENT AND TRADEMARK OFFICE
CERTIFICATE OF CORRECTION

PATENT NO. : 9,682,984 B2
APPLICATION NO. : 14/778461
DATED : June 20, 2017
INVENTOR(S) : Antonio Lorente Bonde-Larsen et al.

Page 1 of 2

It is certified that error appears in the above-identified patent and that said Letters Patent is hereby corrected as shown below:

In the Specification

In Column 11 at Line 18 (approx.), Change "d6)," to --$d_6$),--.

In Column 11 at Line 23 (approx.), Change "d6)," to --$d_6$),--.

In Column 11 at Line 26 (approx.), After "O)" insert --.--.

In Column 11 at Line 36 (approx.), Change "d6)," to --$d_6$),--.

In Column 11 at Line 41 (approx.), Change "d6)," to --$d_6$),--.

In Column 12 at Line 17 (approx.), Change "d6)," to --$d_6$),--.

In Column 12 at Line 23 (approx.), Change "d6)," to --$d_6$),--.

In Column 13 at Line 7 (approx.), Change "d6)," to --$d_6$),--.

In Column 13 at Line 15 (approx.), Change "d6)," to --$d_6$),--.

In Column 14 at Lines 46-49 (approx.), Delete "The solution was cooled to 25° C. and poured into into water (30 ml) at 0/5° C. The pH was adjusted to 9/10 by addition of 50% aqueous NaOH and the product was extracted with dichloromethane." and insert the same on Column 14, Line 47 (approx.), as a new paragraph.

In Column 14 at Line 47 (approx.), Change "into into" to --into--.

In Column 14 at Line 64, Change "d6)," to --$d_6$),--.

In Column 15 at Line 4, Change "d6)," to --$d_6$),--.

Signed and Sealed this
Eleventh Day of June, 2019

Andrei Iancu
*Director of the United States Patent and Trademark Office*

CERTIFICATE OF CORRECTION (continued)
U.S. Pat. No. 9,682,984 B2

In Column 15 at Line 16, Change "d6)," to --$d_6$),--.

In Column 15 at Line 23 (approx.), Change "d6)," to --$d_6$),--.

In Column 15 at Line 36, Change "d6)," to --$d_6$),--.

In Column 15 at Line 42 (approx.), Change "d6)," to --$d_6$),--.

In Column 15 at Line 54, Change "d6)," to --$d_6$),--.

In Column 15 at Line 62 (approx.), Change "d6)," to --$d_6$),--.

In Column 25 at Line 15, Change "d6)," to --$d_6$),--.

In Column 25 at Line 23, Change "d6)," to --$d_6$),--.

In Column 28 at Line 20, Change "d6)," to --$d_6$),--.

In Column 28 at Line 26 (approx.), Change "d6)," to --$d_6$),--.

In the Claims

In Column 30 at Lines 3-15 (Structure), In Claim 10,

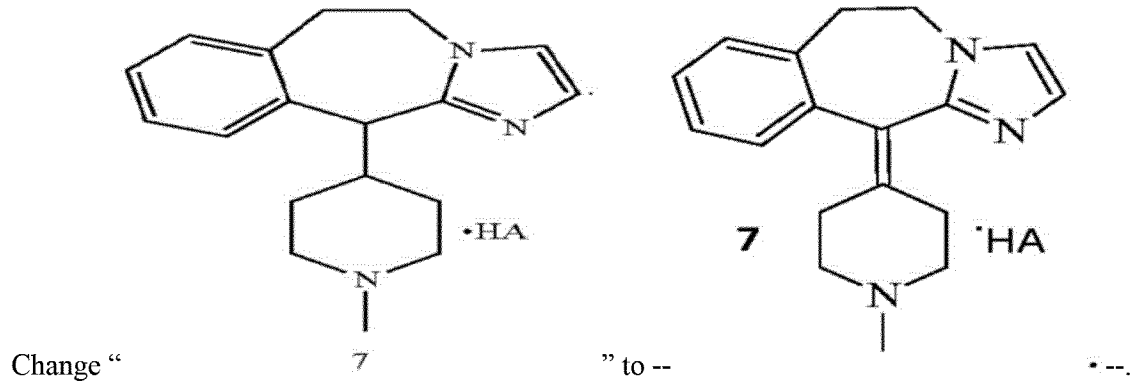

Change " " to -- --.

In Column 30 at Lines 50-60 (Structure), In Claim 12,

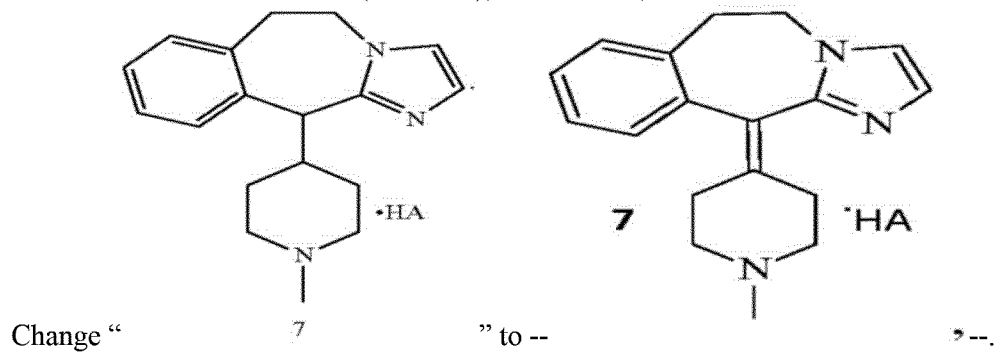

Change " " to -- --.